(12) United States Patent
Mallet et al.

(10) Patent No.: US 6,432,701 B1
(45) Date of Patent: Aug. 13, 2002

(54) DERIVED TYROSINE HYDROXYLASE GENE EXPRESSION SYSTEM

(75) Inventors: Jacques Mallet; Rolando Meloni; Philippe Ravassard, all of Paris; Fabienne Treilhou, Gif sur Yvette, all of (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/171,162
(22) PCT Filed: Apr. 10, 1997
(86) PCT No.: PCT/FR97/00636
§ 371 (c)(1),
(2), (4) Date: Oct. 14, 1998
(87) PCT Pub. No.: WO97/40172
PCT Pub. Date: Oct. 30, 1997

(30) Foreign Application Priority Data

Apr. 25, 1996 (FR) .............................. 96 05223

(51) Int. Cl.⁷ .............................................. C12N 15/00
(52) U.S. Cl. ................................. 435/320.1; 536/24.1
(58) Field of Search ...................... 435/320.1; 536/24.1

(56) References Cited

PUBLICATIONS

Puers et al., Identification of repeat sequence heterogeneity at the polymorphic short tandem repeat locus HUMTHOI (AATG)n and reassignment of alleles in population analysis by using a locus–specific allelic ladder, American Journal of Human Genetics, 53(4), 953–958 (1993).

Edwards et al., Genetic variation at five trimeric and tetrameric tandem repeat loci in four human population groups, Genomics, 12, 241–253 (1992).

Gandelman et al., Species and regional differences in the expression of cell–type specific elements at the human and rat tyrosine hydroxylase gene loci, Journal of Neurochemistry 55(6), 2149–2152 (1990).

Kobayashi et al., Structure of the human tryosine hydroxylase gene: Alternative splicing from a single gene accounts for generation of four mRNA types, Journal of Biochemistry 103(6), 907–912 (1988).

Meloni et al., A tetra–repeat microsatellite, located in the tyrosine hydroxylase gene, presents a rare allele associated with schizophrenia and acts as a transcription activator in vitro, American Journal of Human Genetics, 59(4) A155 (1996).

NCBI reports on tyrosine hydroxylase gene and introns.

Chiba et al., Metabolism vol. 49:1145–1149 (2000).

excerpt of Ausubel et al. Current Protocols in Molecular Biology 1993.

excerpt of Coligan et al. Current Protocols in Immunology 1993.

*Primary Examiner*—Laurie Scheiner
*Assistant Examiner*—Jeffrey S. Parkin
(74) *Attorney, Agent, or Firm*—Wiley Rein & Fielding, LLP

(57) ABSTRACT

The invention discloses a new system for gene expression. The system is based in particular on the use of derived sequences of the first intron of the tyrosine hydroxylase gene having transcription enhancing properties. The system is particularly useful in the production of proteins in vitro, ex vivo or in vivo, particularly in gene therapy applications.

27 Claims, 3 Drawing Sheets

SEQUENCE LISTING

<160> NUMBER OF SEQ ID NOS: 15

<210> SEQ ID NO 1
<211> LENGTH: 636
<212> TYPE: DNA
<213> ORGANISM: Homo sapiens

<400> SEQUENCE: 1

| | | | | | | |
|---|---|---|---|---|---|---|
| cttgaatctt | aacgatcgga | atgtggaaac | aaatccatcc | aaaaaatcca | agatggccag | 60 |
| aggtccccgg | ctgctgcacc | cagcccccac | cctactccca | cctgccctg | cctccctctg | 120 |
| ccccagctgc | cctagtcagc | accccaacca | gcctgcctgc | ttggggaggc | agccccaagg | 180 |
| cccttcccag | gctctagcag | cagctcatgg | tggggggtcc | tgggcaaata | gggggcaaaa | 240 |
| ttcaaagggt | atctgggctc | tggggtgatt | cccattggcc | tgttcctccc | ttatttccct | 300 |
| cattcattca | ttcattcatt | cattcattca | ttcattcacc | atggagtctg | tgttccctgt | 360 |
| gacctgcact | cggaagccct | gtgtacaggg | gactgtgtgg | gccaggctgg | ataatcggga | 420 |
| gcttttcagc | ccacaggagg | ggtcttcggt | gcctccttgg | gcactcagaa | ccttgggctc | 480 |
| cctggcacat | ttaaaatggg | ttttttattta | tggaccttga | ttgaaatgtg | gtgtgagttg | 540 |
| tagcagtgtc | atttccaggt | accttctcag | ggacacaggg | cgccctcccc | cgtcctcccc | 600 |
| cgccctcccc | taccctcccc | caccaggctc | cccatc | | | 636 |

<210> SEQ ID NO 2
<211> LENGTH: 39
<212> TYPE: DNA
<213> ORGANISM: Unknown
<220> FEATURE:
<223> OTHER INFORMATION: oligo derived from HUMTH01

<400> SEQUENCE: 2
tcattcattc attcatcatt cattcattca ttcattcat                          39

<210> SEQ ID NO 3
<211> LENGTH: 20
<212> TYPE: DNA
<213> ORGANISM: Unknown
<220> FEATURE:
<223> OTHER INFORMATION: oligo derived from HUMTH01

<400> SEQUENCE: 3
tcattcatca ttcattcatt                                              20

<210> SEQ ID NO 4
<211> LENGTH: 20
<212> TYPE: DNA
<213> ORGANISM: Unknown
<220> FEATURE:
<223> OTHER INFORMATION: oligo derived from HUMTH01

<400> SEQUENCE: 4

```
aatgaatgaa tgatgaatga                                          20

<210> SEQ ID NO 5
<211> LENGTH: 20
<212> TYPE: DNA
<213> ORGANISM: Unknown
<220> FEATURE:
<223> OTHER INFORMATION: oligo derived from HUMTH01

<400> SEQUENCE: 5
tcattcattc attcattcat                                          20

<210> SEQ ID NO 6
<211> LENGTH: 20
<212> TYPE: DNA
<213> ORGANISM: Unknown
<220> FEATURE:
<223> OTHER INFORMATION: oligo derived from HUMTH01

<400> SEQUENCE: 6
atgaatgaat gaatgaatga                                          20

<210> SEQ ID NO 7
<211> LENGTH: 54
<212> TYPE: DNA
<213> ORGANISM: Unknown
<220> FEATURE:
<223> OTHER INFORMATION: oligo derived from HUMTH01

<400> SEQUENCE: 7
ccctcattca ttcattcatc attcattcat tcattcattc attcaccgcg cgcg    54

<210> SEQ ID NO 8
<211> LENGTH: 54
<212> TYPE: DNA
<213> ORGANISM: Unknown
<220> FEATURE:
<223> OTHER INFORMATION: oligo derived from HUMTH01

<400> SEQUENCE: 8
cgcgcgcggt gaatgaatga atgaatgaat gaatgatgaa tgaatgaatg aggg    54

<210> SEQ ID NO 9
<211> LENGTH: 54
<212> TYPE: DNA
<213> ORGANISM: Unknown
<220> FEATURE:
<223> OTHER INFORMATION: oligo derived from HUMTH01

<400> SEQUENCE: 9
ccctcattca ttcattcatt cattcattca ttcattcatt cattcaccgc gcgc    54

<210> SEQ ID NO 10
<211> LENGTH: 54
<212> TYPE: DNA
<213> ORGANISM: Unknown
<220> FEATURE:
<223> OTHER INFORMATION: oligo derived from HUMTH01

<400> SEQUENCE: 10
gcgcgcggtg aatgaatgaa tgatgaatgt aatgaatgaa tgatgaatg aggg     54

<210> SEQ ID NO 11
<211> LENGTH: 41
<212> TYPE: DNA
```

-continued

```
<213> ORGANISM: Unknown
<220> FEATURE:
<223> OTHER INFORMATION: oligo derived from HUMTH01

<400> SEQUENCE: 11
ccctcattca ttcattcatt cattcattca ttcattcatc c                    41

<210> SEQ ID NO 12
<211> LENGTH: 37
<212> TYPE: DNA
<213> ORGANISM: Unknown
<220> FEATURE:
<223> OTHER INFORMATION: oligo derived from HUMTH01

<400> SEQUENCE: 12
ccctcattca ttcattcatt cattcattca ttcatcc                         37

<210> SEQ ID NO 13
<211> LENGTH: 31
<212> TYPE: DNA
<213> ORGANISM: Unknown
<220> FEATURE:
<223> OTHER INFORMATION: oligo derived from HUMTH01

<400> SEQUENCE: 13
ccctcattca ttcattcatt cattcattca t                               31

<210> SEQ ID NO 14
<211> LENGTH: 29
<212> TYPE: DNA
<213> ORGANISM: Unknown
<220> FEATURE:
<223> OTHER INFORMATION: oligo derived from HUMTH01

<400> SEQUENCE: 14
ccctcattca ttcattcatt cattcatcc                                  29

<210> SEQ ID NO 15
<211> LENGTH: 25
<212> TYPE: DNA
<213> ORGANISM: Unknown
<220> FEATURE:
<223> OTHER INFORMATION: oligo derived from HUMTH01

<400> SEQUENCE: 15
ccctcattca ttcattcatt catcc                                      25
```

DERIVED TYROSINE HYDROXYLASE GENE EXPRESSION SYSTEM

Figure 1:
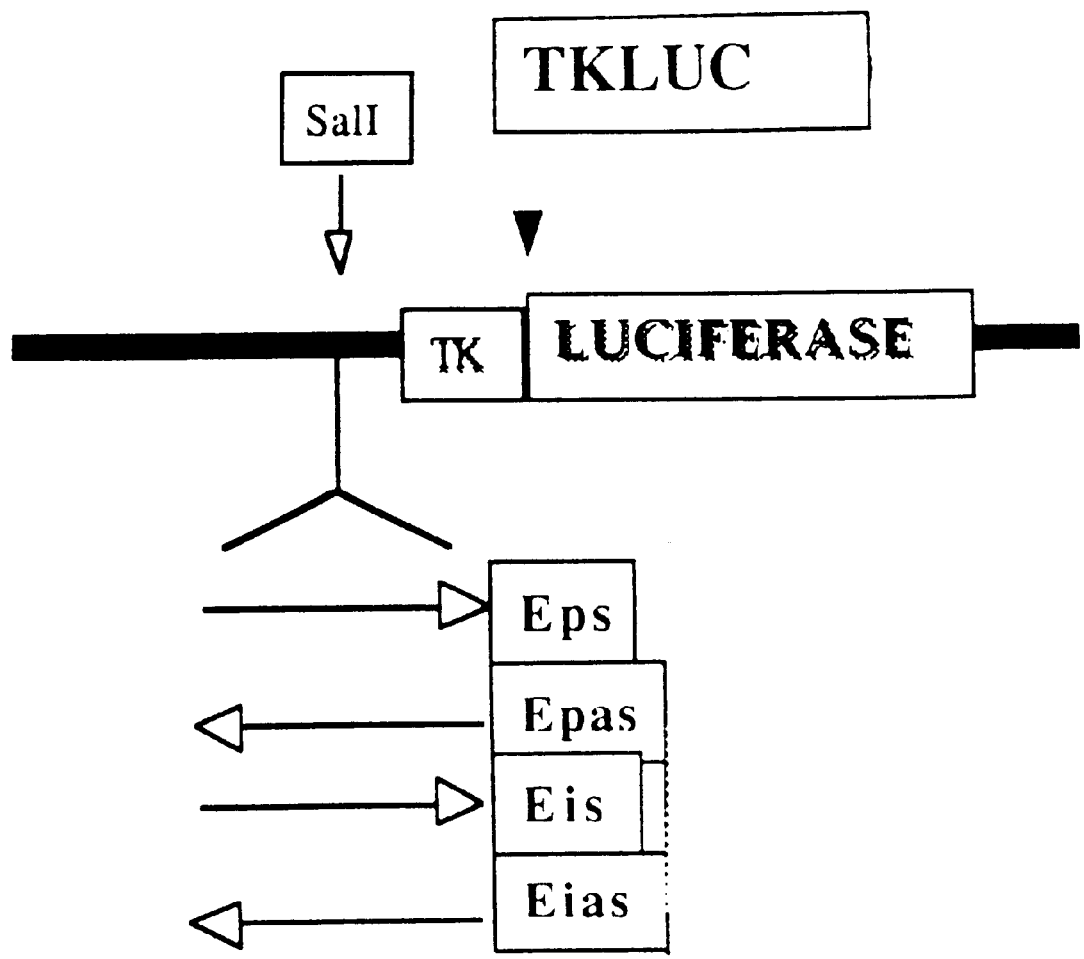

This application was filed under 35 U.S.C. §371 and is the National Stage of International Application No. PCT/FR97/00636, filed Apr. 10, 1997.

The present invention relates to a new system for gene expression. It also relates to the use of this system in gene or cell therapy, for increasing the expression of genes of interest or for producing recombinant proteins.

Gene and cell therapies consist in correcting a deficiency or an abnormality (mutation, aberrant expression, and the like) or in providing for the expression of a protein of therapeutic interest by introducing genetic information into the cell or organ affected. This genetic information may be introduced either ex vivo into a cell extracted from the organ, the modified cell then being reintroduced into the body (cell therapy), or directly in vivo into the appropriate tissue (gene therapy). Different techniques exist for performing gene transfer, including various techniques of transfection involving natural or synthetic chemical or biochemical vectors such as complexes of DNA and DEAE-dextran (Pagano et al., J. Virol. 1 (1967) 891), of DNA and nuclear proteins (Kaneda et al., Science 243 (1989) 375), and of DNA and lipids (Felgner et al., PNAS 84 (1987) 7413), the use of liposomes (Fraley et al., J. Biol. Chem. 255 (1980) 10431), cationic lipids, and the like. Another technique is based on the use of viruses as vectors for gene transfer. In this connection, different viruses have been tested for their capacity to infect certain cell populations, and especially retroviruses (RSV, HMS, MMS, and the like), the HSV virus, adeno-associated viruses and adenoviruses. One of the difficulties in developing these gene and cell therapies lies, however, in the efficacy of the treatment. In particular, it is important to be able to obtain a strong expression of the gene of interest in order to improve the therapeutic effect. The same type of problem arises in the case of methods for the production of recombinant proteins.

Different types of promoters have been described in the literature and are used to control the expression of genes of interest. However, the levels of expression obtained are sometimes insufficient for obtaining industrial amounts of recombinant protein in vitro, or for generating in vivo a substantial and/or lasting therapeutic effect. The present invention now describes a new, especially effective system for the expression of genes. The present invention is the outcome, in particular, of the identification of regions endowed with transcription enhancer activity, enabling the strength of the promoters, and thus the levels of gene expression, to be increased.

The present invention is the outcome, more especially, of the identification of regions of the first intron of the tyrosine hydroxylase gene which are capable of increasing the activity of transcription promoters. These regions are located more precisely in the microsatellite HUMTH01 present in the first intron of this gene.

Microsatellites represent an abundant class of DNA repeat sequences which display great polymorphism linked to variations in the number of repeat motifs and/or in the sequence of these motifs. For this reason, these microsatellites have been used as genetic markers for the construction of genetic maps and for the identification of loci involved in pathologies. The size of the different alleles of a microsatellite depends on variations in the number of repeat motifs. Sequencing experiments on repeat dimers have thus enabled a variation to be shown in the number of repeat motifs and in their sequence. These variations can correspond, in particular, to "perfect" repetitions, that is to say repetitions without interruption in the sequence of bases, or to "imperfect" repetitions containing one or more interruptions in the sequence of motifs, these interruptions entailing deletion(s) or insertion(s). In the same way, variations in length and/or in sequence have also been observed in trimeric or tetrameric repeat motifs. Thus, variations of this type have been observed in the microsatellites HUMHPRTB (Edwards et al., Genomics 12 (1992) 241) and HUMTH01 (Puers et al., Am. J. Hum. Genet. 53 (1993) 953).

The microsatellite HUMTH01 is located in the first intron of the gene for tyrosine hydroxylase (TH), which is the limiting enzyme of the pathway of catecholamine biosynthesis. A portion of the sequence of this intron is shown as SEQ ID No. 1 (from nucleotide 871). This sequence includes the microsatellite HUMTH01 (allele (TCAT)9, shown in bold characters), which is located at position 1170 (GenBank, accession # D00269). The microsatellite HUMTH01 consists of tetrameric TCAT repeat motifs. It displays a certain polymorphism, different alleles having been described possessing variable numbers of repeat motifs. The allele most often encountered (allele Ei) contains 10 repeat motifs and a deletion of one base pair in the fifth repeat motif, which contains the sequence CAT (SEQ ID No. 2). Other alleles have been identified carrying from 5 to 10 TCAT motifs.

The Applicant has now shown that, surprisingly, these sequences are specifically recognized by proteins present in different nuclear extracts (Example 1). Furthermore, the Applicant demonstrated that these sequences enabled gene transcription to be increased in different cell systems (Examples 3 and 4). Thus, in PC12 cells, an increase in transcriptional activity by a factor of 25 to 50 has been observed. In Hela cells, an exceptional increase by a factor of 100 to 350 times has been observed. Hence these sequences display very potent transcription activator properties. These properties are especially unexpected, and far superior to the effects observed with other transcription enhancers. Thus, an increase in transcriptional activity by a factor of 3 to 6 has been observed with HRAS1-VNTR sequences (Green et al., 1993, ref), and by a factor of 2 to 5 with INS-VNTR sequences (Catignani et al., 1995). The increase obtained with the sequences of the invention can exceed a factor of 300, and constitutes an enormous advantage over the previous systems. In addition, the results obtained show that the sequences of the invention are functional in different cell types and in cells of different organisms (PC12 rat cells, HeLa human cells), demonstrating a very broad potential of applications.

Hence, a first subject of the invention relates to a DNA fragment having transcription enhancer activity, consisting essentially of a portion of the first intron of the tyrosine hydroxylase gene. Advantageously, the fragment of the invention comprises less than 200 bp and includes an allele of the microsatellite HUMTH01. More preferably, the fragment comprises less than 100 bp. It is especially advantageous for the fragment to consist essentially of an allele of the microsatellite HUMTH01.

As mentioned above, the microsatellite HUMTH01 is located at position 1170 approximately of the human TH gene (GenBank accession #D00269) and consists mainly of tetrameric TCAT repeat motifs. Different alleles of this microsatellite have been described, possessing variable numbers of repeat motifs (from 5 to 10) and sequence variations, some alleles possessing base mutations. Thus, the allele most often encountered (allele Ei) contains 10 repeat motifs and a deletion of one base pair in the fifth repeat motif, which contains the sequence CAT (SEQ ID No. 2). Other alleles have been identified, carrying from 5 to 10 TCAT motifs (SEQ ID Nos 9–15). In addition, a DNA fragment carrying 3 TCAT motifs may be synthesized and tests as a transcription enhancer, according to the invention.

In this connection, a subject of the invention is also an isolated DNA fragment, characterized in that it possesses transcription enhancer activity and in that it possesses the sequence $(TACT)_n$-$(CAT)_o$-$(TCAT)_p$, in which n is between 1 and 50, o is between 0 and 20 and p is between 0 and 50.

According to a particular variant of the invention, the transcription enhancer possesses a sequence $(TCAT)_n$-$(CAT)_o$-$(TCAT)_p$ in which n is between 2 and 20 inclusive and o and p equal 0.

According to another particular variant of the invention, the transcription enhancer possesses a sequence $(TCAT)_n$-$(CAT)_o$-$(TCAT)_p$ in which n is between 1 and 10, o is between 1 and 5 and p is between 1 and 10.

As a specific example of transcription enhancers according to the invention, there may be mentioned the fragments of sequence SEQ ID Nos 1, 2, 3, 4, 5, 6, 7, 8, 9, 10, 11, 12, 13, 14 and 15.

Another subject of the present invention lies in an expression cassette comprising a coding sequence, a promoter permitting its expression and a transcription enhancer as defined above.

Advantageously, the cassette comprises, in addition, a transcription termination signal.

The promoter is advantageously chosen from promoters which are functional in mammalian, preferably human, cells. The promoter in question can be, in particular, one that permits the expression of a nucleic acid in a hyperproliferative cell (cancer cell, restenosis and the like). In this connection, different promoters may be used, such as the p53 gene promoter. A further option comprises regions of different origin (responsible for the expression of other proteins, or even synthetic sequences). Thus, it is possible to use any promoter or derived sequence that stimulates or represses the transcription of a gene, specifically or otherwise, inducibly or otherwise, strongly or weakly. The promoter sequences of eukaryotic or viral genes may be mentioned in particular. Possible promoter sequences are, for example, ones originating from the genome of the target cell. Among eukaryotic promoters, it is possible to use, in particular, ubiquitous promoters (promoter of the HPRT, PGK, a-actin, tubulin, and the like, genes), promoters of intermediate filaments (promoter of the GFAP, desmin, vimentin, neurofilament, keratin, and the like, genes), promoters of therapeutic genes (for example the promoter of the MDR, CFTR, factor VIII, ApoAI, ApoAII, albumin, thymidine kinase, and the like, genes), tissue-specific promoters (promoter of the pyruvate kinase, villin, intestinal fatty acid binding protein or smooth muscle a-actin gene, neuronal specific enolase promoter (Forss-Petter et al., Neuron 5 (1990) 187); and the like), of the promoter generating the V1 form of the mRNA of VAChT (acetylcholine transporter: Cervini et al., J. Biol. Chem. 270 (1995) 24654) or alternatively promoters that respond to a stimulus (steroid hormone receptor, retinoic acid receptor, and the like). Similarly, the promoter sequences may be ones originating from the genome of a virus, such as, for example, the promoters of the adenovirus E1A and MLP genes, the CMV early promoter or alternatively the RSV or MMTV LTR promoter, the herpesvirus TK gene promoter, and the like. In addition, these promoter regions may be modified by adding or deleting sequences. To this end, the promoter uses can be a "minimal" promoter, that is to say a reduced promoter whose activity depends essentially on the presence of a transactivator such as an enhancer of the invention. As a result, in the absence of the enhancer the activity of the promoter is reduced and the gene is not expressed or is expressed to only a small extent. In contrast, in the presence of the enhancer, the activity of the minimal promoter is strong and the expression of the gene of interest substantial. The minimal promoter generally consists of a TATA or INR box. These elements are, in effect, the minimum elements necessary for the expression of a gene in the presence of a transactivator. It advantageously comprises less than 200 bp, including the TATA or INR region. The minimal promoter may be prepared from any promoter by genetic modification. As a particular example of a candidate promoter, the thymidine kinase gene promoter may be mentioned. Advantageous results have, more precisely, been obtained with a minimal promoter derived from the herpes simplex type I thymidine kinase (TK) gene promoter composed of nucleotides −109 to +52, or −37 to +19. The minimal is promoter may also be derived from human CMV. In particular, it can consist of the fragment lying between nucleotides −53 and +75 or −31 and +75 of CMV (+1 corresponding to the ATG codon). Any conventional promoter may however be used, such as, for example, the promoter of the genes coding for chloramphenicol acetyltransferase, β-galactosidase or alternatively luciferase.

Advantageously, the transcription promoter is a promoter which is functional in mammalian cells, and in particular a viral promoter (TK, CMV), ubiquitous promoter (PGK) or specific promoter (neuronal specific enolase promoter, promoter generating the V1 form of the mRNA of VAChT.

In another preferred embodiment, the transcription promoter is a minimal promoter, composed essentially of a region of less than 200 bp comprising a TATA or INR box.

The coding sequence advantageously comprises one or more sequences coding for proteins. The sequence can be, in particular, one that codes for a therapeutic product, which can be a peptide, polypeptide, protein, ribonucleic acid, and the like. More especially, the coding sequence is a DNA sequence (cDNA, gDNA, synthetic, human, animal, plant, and the like, DNA) coding for a proteinaceous product such as enzymes, blood derivatives, hormones, lymphokines, namely interleukins, interferons, TNF, and the like (FR 92 03120), growth factors, neurotransmitters or their precursors or synthetic enzymes, trophic factors, namely BDNF, CNTF, NGF, IGF, GMF, aFGF, bFGF, NT3, NT5, and the like; apolipoproteins, namely ApoAI, ApoAIV, ApoE, and the like (FR 93 05125), distrophin or a minidystrophin (FR 91 11947), tumour-suppressing genes, namely p53, Rb, Rap1A, DCC, k-rev, and the like (FR 93 04745), genes coding for factors involved in coagulation, namely factors VII, VIII, IX, and the like, or alternatively all or part of a natural or artificial immunoglobulin (Fab, ScFv, and the like), a ligand RNA (WO91/19813), and the like.

The coding sequence can also be an antisense sequence, whose expression in the target cell enables gene expression or the transcription of cellular mRNAs to be controlled. Such sequences can, for example, be transcribed in the target cell into RNAs complementary to cellular mRNAs and can thus block their translation into protein, according to the technique described in Patent EP 140,308.

The present invention is also suited to the expression of sequences coding for toxic factors. The latter can be, in particular, cell poisons (diphtheria toxin, pseudomonas toxin, ricin A, and the like), a product inducing sensitivity to an external agent (suicide genes: thymidine kinase, cytosine deaminase, and the like) or alternatively killer genes capable of inducing cell death (Grb3-3 (PCT/FR94/00542), anti-ras ScFv (WO94/29446), and the like. This system is also especially advantageous for the expression of cytokines, interferons, TNF or TGF, for example.

The expression cassette advantageously consists of the following elements:
- as enhancer region, a sequence $(TCAT)_n$-$(CAT)_o$-$(TCAT)_p$, in which is not between 1 and 50, o is between 0 and 20, and p is between 0 and 50,
- as promoter, the HSV-1 virus thymidine kinase gene promoter or a minimal promoter derived therefrom, the CMV early promoter or a minimal promoter derived therefrom, the PGK promoter, the specific enolase promoter or the VAChT gene promoter,
- a coding sequence of interest.

Still more preferably, the promoter consists of the region −109 to +52 or −37 to +19 of the HSV-1 thymidine kinase gene promoter.

Advantageously, the enhancer region is chosen from the fragments of sequence SEQ ID Nos 1, 2, 3, 4, 5, 6, 7, 8, 9, 10, 11, 12, 13, 14 and 15. In addition, an especially noteworthy property of the enhancer regions of the invention is that they appear to be active both in the sense orientation (normal orientation of the microsatellite in the TH gene) and in the antisense orientation (reverse orientation to that of the microsatellite in the TH gene). As a result, in the expression cassettes of the invention, the enhancer region may be positioned in both orientations (5'→3' or 3'→5').

Another aspect of the invention also lies in an expression vector comprising an expression cassette as defined above. The vector may be of the plasmid or viral kind.

Among viral vectors, adenoviruses, retroviruses, herpesviruses or alternatively adeno-associated viruses may be mentioned more preferentially. The viruses according to the present invention are defective, that is to say incapable of replicating autonomously in the target cell. Generally, the genome of the defective viruses used in the context of the present invention hence lacks at least the sequences necessary for the replication of the said virus in the infected cell. These regions may be either removed (wholly or partially), or rendered non-functional, or replaced by other sequences, and in particular by the sequences of the invention. Preferably, the defective virus nevertheless retains the sequences of its genome which are necessary for encapsidation of the viral particles.

As regards adenoviruses more especially, different serotypes, the structure and properties of which vary somewhat, have been characterized. Among these serotypes, it is preferable to use, in the context of the present invention, human adenoviruses type 2 or 5 (Ad 2 or Ad 5) or adenoviruses of animal origin (see Application WO94/26914). Among adenoviruses of animal origin which can be used in the context of the present invention, adenoviruses of canine, bovine, murine (e.g.: Mav1, Beard et al., Virology 75 (1990) 81), ovine, porcine, avian or alternatively simian (e.g.: SAV) may be mentioned. Preferably, the adenovirus of animal origin is a canine adenovirus, and more preferably a CAV-2 adenovirus [strain Manhattan or A26/61 (ATCC VR-800), for example]. It is preferable to use adenoviruses of human or canine or mixed origin in the context of the invention.

Preferably, the genome of the recombinant adenoviruses of the invention comprises at least the ITRs and the encapsidation region of an adenovirus, and the nucleic acid sequence coding for a chimeric molecule and an expression cassette as are defined above. More preferably, in the genome of the adenoviruses of the invention, the E1 region at least is non-functional. The viral gene in question may be rendered non-functional by any technique known to a person skilled in the art, and in particular by total elimination, replacement (for example by the sequences of the invention), partial deletion or addition of one or more bases in the gene or genes in question. Such modifications may be obtained in vitro (on the isolated DNA) or in situ, for example by means of genetic engineering techniques, or alternatively by treatment by means of mutagenic agents. Other regions may also be modified, and in particular the E3 (WO95/02697), E2 (WO94/28938), E4 (WO94/28152, WO94/12649, WO95/02697) and L5 (WO95/02697) regions. According to a preferred embodiment, the adenovirus according to the invention comprises a deletion in the E1 and E4 regions. According to another preferred embodiment, it comprises a deletion in the E1 region, into which are inserted the E4 region and the sequences of the invention (see FR94 13355).

The defective recombinant adenoviruses according to the invention may be prepared by any technique known to a person skilled in the art (Levrero et al., Gene 101 (1991) 195, EP 185,573; Graham, EMBO J. 3 (1984) 2917). In particular, they may be prepared by homologous recombination between an adenovirus and a plasmid carrying, inter alia, the expression cassette of the invention and sequences homologous to the adenovirus. Homologous recombination takes place after cotransfection of the said adenovirus and said plasmid into a suitable cell line. The adenoviral genome may also be prepared in vitro, in a bacterium (FR95 01632) or in a yeast (WO95/03400). The cell line used for the production of the adenoviruses should preferably (i) be transformable by the said elements, and (ii) contain the sequences capable of complementing the portion of the genome of the defective adenovirus, preferably in integrated form in order to avoid risks of recombination. As an example of a line, there may be mentioned the human embryonic kidney line 293 (Graham et al., J. Gen. Virol. 36 (1977) 59) which contains, in particular, integrated in its genome, the left-hand portion of the genome of an Ade5 adenovirus (12%), or lines capable of complementing the E1 and E4 functions as are described, in particular, in Applications Nos WO94/26914 and WO95/02697.

Thereafter, the adenoviruses which have multiplied are recovered and purified according to standard techniques of molecular biology, as illustrated in the examples.

Adeno-associated viruses (AAV) are, for their part, relatively small DNA viruses which integrate stably and in a site-specific manner in the genome of the cells they infect. They are capable of infecting a broad range of cells without inducing an effect on cell growth, morphology or differentiation. Moreover, they do not appear to be implicated in pathologies in man. The AAV genome has been cloned, sequenced and characterized. It comprises approximately 4,700 bases, and contains at each end an inverted repeat region (ITR) of approximately 145 bases, serving as origin of replication for the virus. The remainder of the genome is divided into 2 essential regions carrying the encapsidation functions: the left-hand portion of the genome, which contains the rep gene involved in viral replication and the expression of the viral genes; and the right-hand portion of the genome, which contains the cap gene coding for the capsid proteins of the virus.

The use of vectors derived from AAV for the transfer of genes in vitro and in vivo has been described in the literature (see, in particular, WO91/18088; WO93/09239; U.S. Pat. Nos. 4,797,368, 5,139,941, EP 488,528). These applications describe different constructions derived from AAV, in which the rep and/or cap genes are deleted and replaced by a gene of interest, and their use for transferring the said gene of interest in vitro (to cells in culture) or in vivo (directly into a body). The defective recombinant AAVs according to the invention may be prepared by cotransfection, into a cell line infected with a human helper virus (for example an adenovirus), of a plasmid containing the expression cassette of the invention flanked by two inverted repeat regions (ITR) of AAV, and a plasmid carrying the encapsidation genes (rep and cap genes) of AAV. The recombinant AAVs produced are then purified by standard techniques.

Regarding herpes viruses and retroviruses, the construction of recombinant vectors has been amply described in the literature: see, in particular, Breakfield et al., New Biologist 3 (1991) 203; EP 453242, EP 178220, Bernstein et al., Genet. Eng. 7 (1985) 235; McCormick, BioTechnology 3 (1985) 689, and the like.

In particular, retroviruses are integrative viruses which selectively infect dividing cells. They hence constitute vectors of interest for cancer applications. The retrovirus genome essentially comprises two LTRS, an encapsidation sequence and three coding regions (gag, pol and env). In the recombinant vectors derived from retroviruses, the gag, pol and env genes are generally deleted wholly or partially, and replaced by a heterologous nucleic acid sequence of interest. These vectors may be produced from different types of retrovirus such as, in particular, MoMuLV (Moloney murine leukaemia virus; also designated MOMLV), MSV (Moloney murine sarcoma virus), HaSV (Harvey sarcoma virus), SNV (spleen necrosis virus), RSV (Rous sarcoma virus) or alternatively Friend virus.

To construct recombinant retroviruses according to the invention, a plasmid containing, in particular, the LTRS, the encapsidation sequence and the sequences of the invention (expression cassette) is generally constructed, and then used to transfect a so-called encapsidation cell line capable of supplying in trans the retroviral functions which are deficient in the plasmid. Generally, the encapsidation lines are hence capable of expressing the gag, pol and env genes. Such encapsidation lines have been described in the prior art, and in particular the line PA317 (U.S. Pat. No. 4,861,719), the line PsiCRIP (WO90/02806) and the line GP+envAm-12 (WO89/07150). Moreover, the recombinant retroviruses can contain modifications in the LTRs to eliminate transcriptional activity, as well as extended encapsidation sequences containing a portion of the gag gene (Bender et al., J. Virol. 61 (1987) 1639). The recombinant retroviruses produced are then purified by standard techniques.

The expression cassette may also be inserted into a plasmid vector (FR95 02117).

The gene expression system of the invention is especially suitable for use in gene or cell therapy, or for producing recombinant proteins. For gene or cell therapy applications, the cassettes or plasmid vectors may be used in the form of naked DNA or DNA complex has inert transfer vectors. Different types of inert vectors capable of promoting the transfer of nucleic acids into eukaryotic cells and their expression therein have, in effect, been described. Chemical or biochemical vectors represent an alternative to viruses, especially for reasons of convenience and safety and also on account of the absence of theoretical limit regarding the size of the DNA to be transfected.

These synthetic vectors have two main functions, to compact the nucleic acid which is to be transfected and to promote its binding to the cell as well as its passage through the plasma membrane and, where appropriate, both nuclear membranes. To compensate for the polyanionic nature of nucleic acids, non-viral vectors all possess polycationic charges.

Among the synthetic vectors developed, the most advantageous are cationic polymers of the polylysine, (LKLK)n, (LKKL)n, polyethylenimine (WO96/02655) and DEAE-dextran type, or alternatively lipofectants or cationic lipids. They possess the property of condensing DNA and of promoting its combination with the cell membrane. Among the latter compounds, there may be mentioned lipopolyamines (lipofectamine, transfectam, WO95/18863) and various cationic or neutral lipids (DOTMA, DOGS, DOPE, and the like). More recently, the concept of receptor-mediated, targeted transfection has been developed, which turns to good account the principle of condensing DNA by means of the cationic polymer while directing the binding of the complex to the membrane as a result of a chemical coupling between the cationic polymer and the ligand for a membrane receptor present at the surface of the cell type which it is desired to graft. Targeting of the transferrin or insulin receptor or of the asialoglycoprotein receptor of hepatocytes has thus been described.

A subject of the present invention is also any pharmaceutical composition comprising a vector as defined above. These compositions may be formulated with a view to topical, oral, parenteral, intranasal, intravenous, intramuscular, subcutaneous, intraocular, and the like, administration. Preferably, the composition according to the invention contains vehicles which are pharmaceutically acceptable for an injectable formulation. These can be, in particular, sterile, isotonic saline solutions (monosodium or disodium phosphate, sodium, potassium, calcium or magnesium chloride, and the like, or mixtures of such salts), or dry, in particular lyophilized, compositions which, on adding sterilized water or physiological saline, as the case may be, enable injectable solutions to be formed. In the case of retroviruses, it can be advantageous to use directly the encapsidation cells or cells infected ex vivo with a view to their reimplantation in vivo, where appropriate in the form of neo-organs (WO94/24298).

The doses of vector used for the injection may be adjusted in accordance with different parameters, and in particular in accordance with the mode of administration used, the pathology in question or the desired period of treatment. Generally speaking, the recombinant viruses according to the invention are formulated and administered in the form of doses of between $10^4$ and $10^{14}$ pfu/ml. For AAV and adenoviruses, doses of $10^6$ to $10^{10}$ pfu/ml may also be used. The term pfu (plaque forming unit) corresponds to the infectious power of a suspension of virions, and is determined by infecting a suitable cell culture and measuring, generally after 48 hours, the number of plaques of infected cells. The techniques for determining the pfu titre of a viral solution are well documented in the literature.

Another subject of the invention consists of a cell comprising a DNA fragment, an expression cassette or a vector as are defined above. These cells are obtained by any technique known to a person skilled in the art that enables a DNA to be introduced into a given cell. The technique may comprise, in particular, transformation, transfection, infection, electroporation, conjugation, protoplast fusion or any other technique known to a person skilled in the art. As regards transformation in vitro or ex vivo, different protocols have been described in the prior art. In particular, cell transformation may be carried out by treating whole cells in the presence of lithium acetate and polyethylene glycol according to the technique described by Ito et al. (J. Bacteriol. 153 (1983) 163–168), or in the presence of ethylene glycol and dimethyl sulphoxide according to the technique of Durrens et al. (Curr. Genet. 18 (1990) 7). An alternative protocol has also been described in Patent Application EP 361,991. Where electroporation is used, it may be carried out according to Becker and Guarentte (in: Methods in Enzymology Vol194 (1991) 182).

The cells according to the invention may be of different origins. In particular, they can comprise bacteria or eukaryotic cells (yeasts, animal cells, plant cells), and the like. Among bacteria, E. coli, B. subtilis, Streptomyces, Pseudomonas (P. putida, P. aeruginosa), Rhizobium meliloti, Agrobacterium tumefaciens, Staphylococcus aureus, Streptomyces pristinaespiralis, Enterococcus faecium or Clostridium, and the like, may be mentioned more preferentially. Among bacteria, it is preferable to use E. coli. Among yeasts, Kluyveromyces, Saccharomvces, Pichia, Hansenula, and the like, may be mentioned. Among mammalian animal cells, CHO, COS, NIH3T3, PC12, and the like, cells may be mentioned. For ex vivo gene therapy applications, haematopoietic stem cells (WO88/08450, WO93/20195, WO93/09815, WO93/11230), endothelial cells (WO89/05345, WO90/06757, WO92/09222), myoblasts (WO93/03768, WO93/24151, WO94/01129), fibroblasts (U.S. Pat. No. 5,219,740, WO89/02468, WO94/07906), hepatocytes (WO89/07136, WO92/12242, WO93/03142), astrocytes (WO94/01135), neuroblasts (WO94/10292, WO94/16059), keratinocytes (WO94/11011) and macrophages (FR93/10222) may also be mentioned. These cells generally possess the capacity to produce a product of therapeutic interest, and may be implanted in vivo. Among blood cells, erythrocytes, neutrophilic, basophilic and eosinophilic granulocytes, B and T lymphocytes, in particular CD4 lymphocytes., cytotoxic lymphocytes (CD8 CTL), tumour infiltrating lymphocytes (TIL) and LAKs, monocytes and macrophages, dendritic cells, megakaryocytes and platelets may be mentioned.

The present application will be described in greater detail by means of the examples which follow, which must be regarded as illustrative and non-limiting.

LEGEND TO THE FIGURES

FIG. 1: Diagram of the plasmid pTK-Luc; Thymidine kinase minimal promoter; Perfect repeat, sense orientation of the TH intron; Perfect repeat, antisense; Imperfect repeat, sense orientation of the TH intron; Imperfect repeat, antisense.

Figure 2:
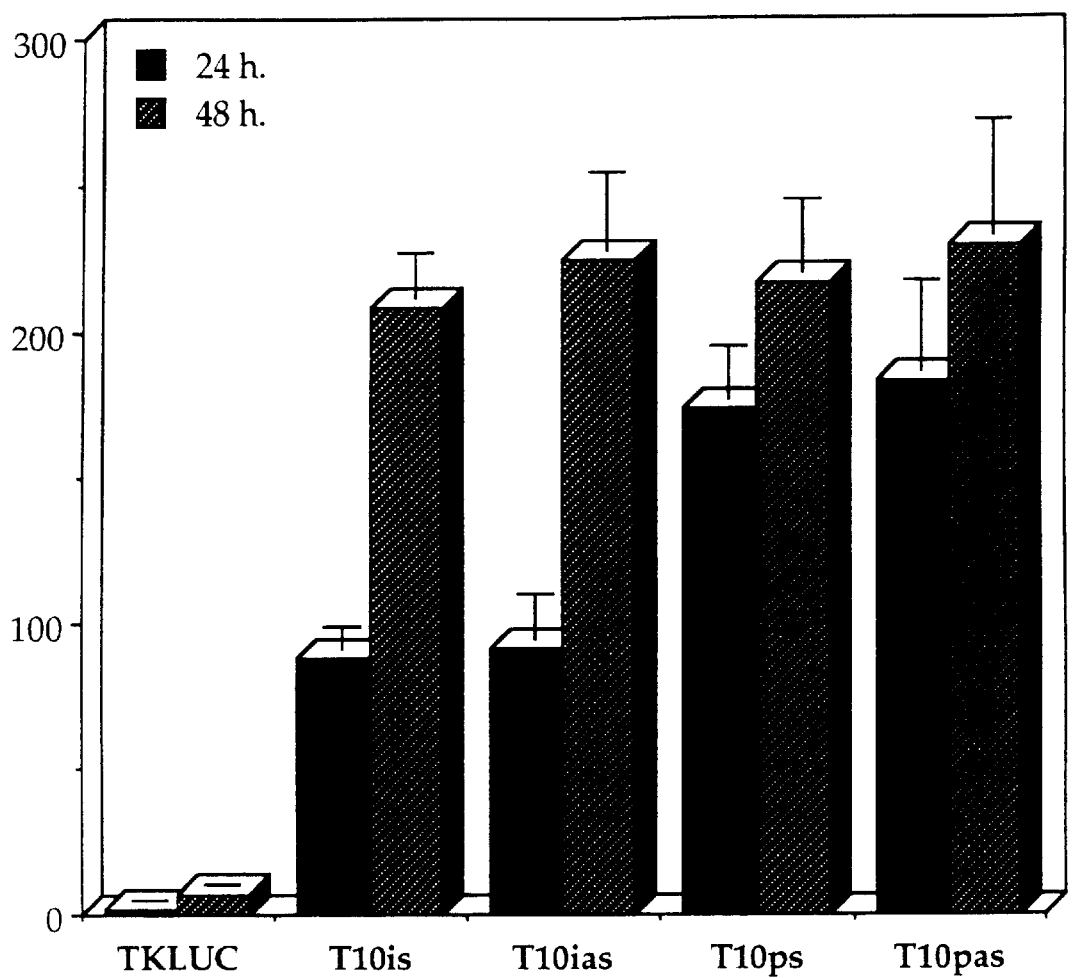

FIG. 2: Luciferase activity in transformed Hela cells.

Figure 3:
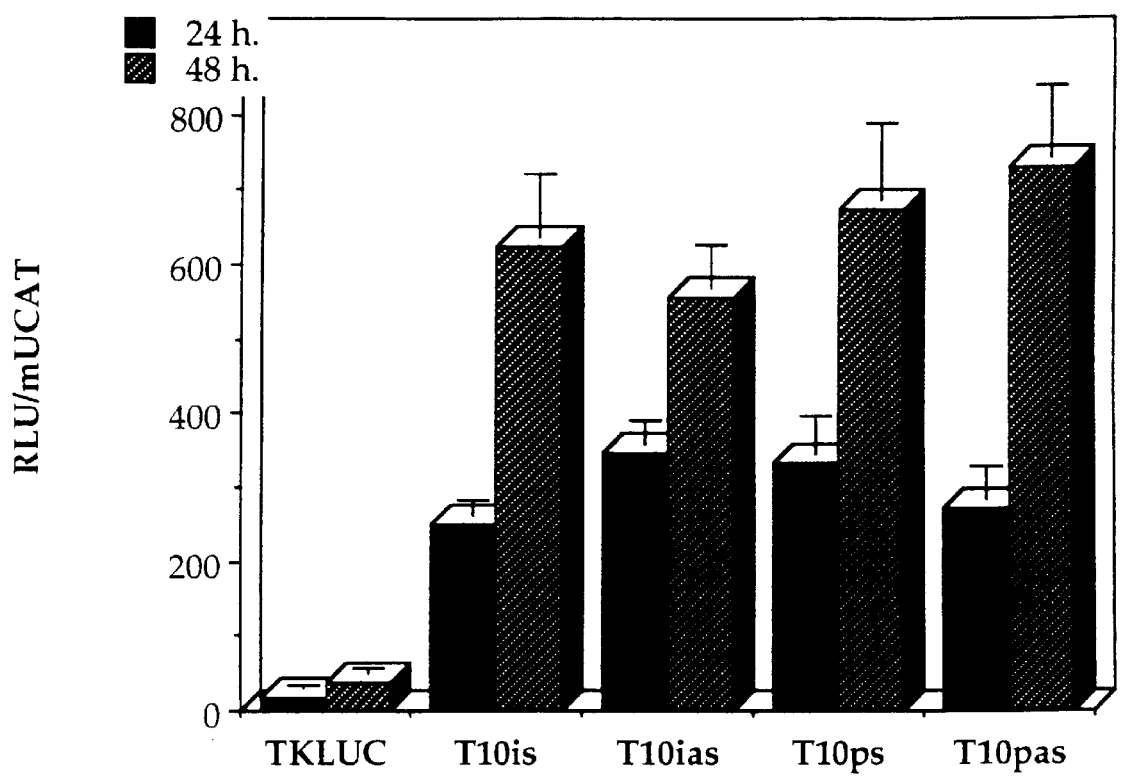

FIG. 3: Luciferase activity in transformed PC12 cells.

GENERAL TECHNIQUES OF MOLECULAR BIOLOGY

The methods traditionally used in molecular biology, such as centrifugation of plasmid DNA in a caesium chloride/ethidium bromide gradient, digestion with restriction enzymes, gel electrophoresis, transformation in E. coli, precipitation of nucleic acids, and the like, are described in the literature (Maniatis et al., 1989).

Enzymes were supplied by New England Biolabs (Beverly, Mass.).

For the ligations, the DNA fragments are separated according to their size on 0.8 to 1.5% agarose gels, purified with GeneClean (BIO101, LaJolla Calif.) and incubated overnight at 14° C. in 50 mM Tris-HCl buffer pH 7.4, 10 mM $MgCl_2$, 10 mM DTT, 2 mM ATP, in the presence of phage T4 DNA ligase.

Amplification by PCR (polymerase chain reaction) was also carried out according to Maniatis et al., 1989, with the following specifications:

$MgCl_2$ concentration brought to 8 mM;

Denaturation temperature 95° C., hybridization temperature 55° C., elongation temperature 72° C. This cycle was repeated 25 times in a PE9600 Thermalcycler (Perkin Elmer, Norwalk Conn.).

Oligonucleotides are synthesized using phosphoramidite chemistry with the latter derivatives protected at the β position by a cyanoethyl group (Sinha et al., 1984, Giles 1985), employing an Applied Biosystem model 394 automatic DNA synthesizer (Applied Biosystem, Foster City Calif.), according to the manufacturer's recommendations.

Sequencing was performed on double-stranded templates by the chain termination method using fluorescent primers. We used the Taq Dye Primer Kit sequencing kit from Applied Biosystem (Applied Biosystem, Foster City Calif.) according to the manufacturer's specifications.

EXAMPLES

Example 1

Interaction with Nuclear Proteins

The possible involvement of the microsatellite HUMTH01 in the regulation of gene expression was studied by gel retardation experiments (electrophoretic mobility test, EMSA). For this purpose, nuclear extracts of Hela cells were prepared and incubated in the presence of oligonucleotides corresponding to sequences of the microsatellite HUMTH01.

The nuclear extracts of Hela cells were prepared according to the method of Dignam (NAR 11 (1983) 1474), and the protein concentrations according to the technique of Bradford (Anal. Biochem. 72 (1976) 248). The electrophoretic mobility test was carried out in a final volume of 10 µl, in the presence of 10 to 15 µg of nuclear extract incubate for 5 min in the presence of 1 µg of poly(dI-dC)-(dI-dC), in 4 mM HEPES buffer, pH 7.6, 100 mM KCl, 12% glycerol. 25 fmol of double-stranded oligonucleotides labelled with [γ-$^{32}$P]ATP by means of T4 polynucleotide kinase (Amersham) were then incubated for 5 min with the proteins at room temperature. The oligonucleotides used are probes corresponding to the alleles Ei and Ep of the microsatellite HUMTH01. For the competitive experiments, the unlabelled oligonucleotides were added 5 min before the labelled probes. The sequence of the oligonucleotides is as follows:

Ei-sense: TCATTCATCA TTCATTCATT (SEQ ID No. 3)

Ei-as: AATGAATGAA TGATGAATGA (SEQ ID No. 4)

Ep-sense: TCATTCATTC ATTCATTCAT (SEQ ID No. 5)

Ep-As: ATGAATGAAT GAATGAATGA (SEQ ID No. 6)

The DNA-protein complexes formed were then resolved by electrophoresis on non-denaturing 6% acrylamide gel in 0.5×TBE buffer has 4C. After drying, the gels are autoradiographed overnight at room temperature.

The results obtained show that both oligonucleotides are recognized by proteins of the nuclear extract. Moreover, the specificity of the interaction was demonstrated in a competitive experiment with cold oligonucleotides, demonstrating a dose-dependent binding. These results hence clearly demonstrate that nuclear factors interact with the microsatellite HUMTH01.

In a second step, a series of competitive experiments with different oligonucleotides was carried out. The oligonucleotides used correspond to the factor AP1 binding sequence TRE (TGACTCA). The results obtained show that this oligonucleotide does not displace the binding of the oligonucleotides Ei and Ep to the nuclear factors. This indicates that the factors that bind the microsatellite HUMTH01 are different from Jun and Fos. Competitive experiments were also carried out with oligonucleotides containing other protein binding sequences: CRE-TH; CRE; Pou; SP1; AP4 and E-TH. None of these sequences, in 100-fold molar excess, enabled the binding of the nuclear extracts of Hela to the oligonucleotides of the microsatellite to be displaced, confirming the specificity of the interaction.

Example 2

Construction of Expression Cassettes and Vectors 2.1 Synthesis of the Enhancer Regions Different enhancer regions were synthesized in the form of double-stranded oligonucleotides. The oligonucleotides were synthesized on a Beckman Oligo 1000 synthesizer according to the manufacturer's recommendations. The enhancers produced are the following:

T10i-sense (SEQ ID No. 7):
CCCTCATTCA TTCATTCATC ATTCATTCAT TCATTCATTC ATTCACCGCG CGCG This DNA fragment comprises the imperfect allele of the microsatellite HUMTH01, in the sense orientation (normal orientation in the TH intron).

T10i-as (SEQ ID No. 8):
CGCGCGCGGT GAATGAATGA ATGAATGAAT GAATGATGAA TGAATGAATG AGGG

This DNA fragment comprises the imperfect allele of the microsatellite HUMTH01, in the antisense orientation (reverse orientation to the TH intron).

T10p-sense (SEQ ID No. 9):
CCCTCATTCA TTCATTCATT CATTCATTCA TTCATTCATT CATTCACCGC GCGC This DNA fragment comprises the perfect allele of the microsatellite HUMTH01 ((TCAT)$_{10}$).

T10p-as (SEQ ID No. 10):
GCGCGCGGTG AATGAATGAA TGAATGAATG AATGAATGAA TGAATGAATG AGGG

T9-sense (SEQ ID No. 11):
CCCTCATTCA TTCATTCATT CATTCATTCA TTCATTCATC C

T8-sense (SEQ ID No. 12):
CCCTCATTCA TTCATTCATT CATTCATTCA TTCATCC

T7-sense (SEQ ID No. 13):
CCCTCATTCA TTCATTCATT CATTCATTCA TCC

T6-sense (SEQ ID No. 14):
CCCTCATTCA TTCATTCATT CATTCATCC

T5-sense (SEQ ID No. 15):
CCCTCATTCA TTCATTCATT CATCC 2.2. Construction of Vectors 2.2.1 Vector Comprising a TK Promoter A vector comprising a heterologous gene (luciferase) under the control of a TK promoter, as well as an enhancer according to the invention, was constructed. For this purpose, the plasmid pTK-Luc (DeThe et al., Nature 343 (1990) 177) was used. This vector comprises a modified (minimal) TK promoter comprising nucleotides −109 to +52. A similar construction is carried out with a smaller fragment (nucleotides −37 to +19). Different enhancer regions were introduced into this plasmid, upstream of the TK promoter. More especially, the 54-mer enhancers described in Example 2.1. were subcloned into plasmid pTK-Luc by ligation of blunt ends in the SalI site. The insertion and orientation of the inserts was checked by sequencing. The structure of the expression cassettes of the resulting vector is presented in FIG. 1. It is understood that the enhancer regions of the invention may also be positioned downstream of the promoter and of the gene of interest.

2.2.2. Vector Comprising Another Promoter

The vector described above may be readily modified in order to replace the TK promoter by any other desired transcription promoter, such as the CMV early promoter or any minimal promoter derived therefrom, such as a promoter consisting of the fragment lying between nucleotides −53 and +75 or −31 and +75 of CMV. Other possibilities are the murine or human PGK gene promoter, the neuronal specific enolase promoter or the promoter promoter generating the V1 form of the mRNA of VAChT. Moreover, different vectors or cassettes carrying these different promoters have been described in the literature. It is thus possible to construct vectors or cassettes of the invention by inserting an enhancer sequence into these constructions (Forss-Petter et al., Neuron 5 (1990) 187; Cervini et al., J. Biol. Chem. 270 (1995) 24654; and the like).

2.2.3. Plasmid RSV-CAT

The plasmid RSV-CAT was used in the experiments to determine the efficacy of cell transfection. This plasmid was hence cotransfected with the vectors of the invention. This plasmid comprises the CAT gene under the control of the RSV virus LTR. Its construction has been described in Gorman et al. (Science 221 (1983) 551).

Example 3

Effect on Gene Expression in HeLa Cells

This example describes a study of the activity of the sequences of the invention with respect to the levels of gene expression in cells of a carcinoma. The cells studied are Hela cells. They are cells that originate from a human epithelial carcinoma. These cells have been deposited at the ATCC under the reference ATCC CCL-2.

The Hela cells were cultured in Dulbecco medium supplemented with 7% of Supreme serum. $10^6$ cells were taken up in 0.15 ml of serum-free medium and transfected by electroporation using a Biorad "Gene Pulser", with 1 pmol of each vector to be tested, 5 pmol of vehicle (Bluescript II) DNA and 0.5 pmol of plasmid RSV-CAT-enabling the efficacy-of transfection to be evaluated. The cells were harvested 24 and 48 hours after transfection and tested in triplicate for luciferase activity. For this purpose, a LUMAT LB9501 luminometer (Berthold) was used, with a reaction volume of 150 $\mu$l (0.08 mM luciferin; 0.1 mM ATP; 25 mM Tris-phosphate pH 7.8; 8 mM MgCl2; 2 mM dithiothreitol; 1 mM EDTA; 1 Triton; 15% glyceral). The luciferase activity of each vector was then normalized to the CAT activity resulting from the cotransfected vector RSV-CAT. The CAT activity was measured by liquid scintillation counting. The normalized luciferase activity is expressed in RLU (relative light units). The results given are the means of three experiments.

The results obtained are presented in FIG. 2. They show that the sequences T10i and T10p both induce a strong increase in the expression of the gene. Thus, after 24 hours, the sequence T10i induces an increase in the luciferase activity by a factor of 90, and the sequence T10p by a factor of 160. The observed increase is by a factor of approximately 250 for both sequences when they are arranged in the reverse orientation. After 48 hours, the observed increase in the levels of expression is approximately 300- to 350-fold for both sequences in both orientations.

Example 4

Effect on Gene Expression in PC12 Cells

This example describes a study of the activity of the sequences of the invention with respect to the levels of gene expression in the cells of a rat phaeochromocytome. The cells studied are PC12 cells, deposited at the ATCC under the reference ATCC CRL-1721.

The PC12 cells were cultured in RPMI medium supplemented with 10% of horse serum and 5 of foetal calf serum. The protocol of transfection and of measurement of the activity is identical to that used in Example 3 for Hela cells.

The results obtained are presented in FIG. 3. They show that the sequences T10i and T10p induce, irrespective of their orientation, an increase in the expression of the gene by a factor of 25 after 24 hours and by a factor of 50 after 48 hours.

What is claimed is:

1. An expression cassette comprising a transcriptional promoter, a coding sequence, and a transcriptional enhancer consisting of a DNA fragment having the nucleotide sequence $(TCAT)_n$-$(CAT)_o$-$(TCAT)_p$, where n is between 1 and 50, o is between 0 and 20, and p is between 0 and 50.

2. The expression cassette of claim 1, wherein the transcriptional promoter is functional in mammalian cells.

3. The expression cassette of claim 2, wherein the transcriptional promoter is a viral, ubiquitous or tissue-specific promoter.

4. The expression cassette of claim 2, wherein the transcriptional promoter comprises a TATA or INR region.

5. The expression cassette of claim 1, wherein the transcriptional enhancer is in the sense orientation.

6. The expression cassette of claim 1, wherein the transcriptional enhancer is in the antisense orientation.

7. An expression vector comprising an expression cassette according to claim 1.

8. The expression vector of claim 7, which is a plasmid vector.

9. The expression vector of claim 7, which is a viral vector.

10. An expression cassette comprising a transcriptional promoter, a coding sequence, and a transcriptional enhancer consisting of a DNA fragment having the nucleotide sequence of the first intron of a tyrosine hydroxylase gene.

11. The expression cassette of claim 10, wherein the transcriptional promoter is functional in mammalian cells.

12. The expression cassette of claim 11, wherein the transcriptional promoter is a viral, ubiquitous or tissue-specific promoter.

13. The expression cassette of claim 11, wherein the transcriptional promoter comprises a TATA or INR region.

14. The expression cassette of claim 10, wherein the transcriptional enhancer is in the sense orientation.

15. The expression cassette of claim 10, wherein the transcriptional enhancer is in the antisense orientation.

16. An expression vector comprising an expression cassette of claim 10.

17. The expression vector of claim 16, which is a plasmid vector.

18. The expression vector of claim 16, which is a viral vector.

19. An expression cassette comprising a transcriptional promoter, a coding sequence, and a transcriptional enhancer consisting of a DNA fragment having a nucleotide sequence of an allele of the microsatellite HUMTH01 sequence.

20. The expression cassette of claim 19, wherein the transcriptional promoter is functional in mammalian cells.

21. The expression cassette of claim 20, wherein the transcriptional promoter is a viral, ubiquitous or tissue-specific promoter.

22. The expression cassette of claim 20, wherein the transcriptional promoter comprises a TATA or INR region.

23. The expression cassette of claim 19, wherein the transcriptional enhancer is in the sense orientation.

24. The expression cassette of claim 19, wherein the transcriptional enhancer is in the antisense orientation.

25. An expression vector comprising an expression cassette of claim 19.

26. The expression vector of claim 25, which is a plasmid vector.

27. The expression vector of claim 25, which is a viral vector.

* * * * *